US012668633B2

(12) United States Patent
Zhao et al.

(10) Patent No.: US 12,668,633 B2
(45) Date of Patent: Jun. 30, 2026

(54) BIFUNCTIONAL PROTEIN AGAINST PD-1 AND TGF-β

(71) Applicant: CHIA TAI TIANQING PHARMACEUTICAL GROUP CO., LTD., Lianyungang City (CN)

(72) Inventors: Wei Zhao, Lianyungang City (CN); Yingchun Li, Lianyungang City (CN); Haili Lv, Lianyungang City (CN); Lianxiang Xie, Lianyungang City (CN); Zhewen Zhang, Lianyungang City (CN); Yu Qin, Lianyungang City (CN); Xiquan Zhang, Lianyungang City (CN); Yanju Cheng, Lianyungang City (CN); Peng Lv, Lianyungang City (CN); Tiantian Li, Lianyungang City (CN)

(73) Assignee: CHIA TAI TIANQING PHARMACEUTICAL GROUP CO., LTD., Lianyungang City (CN)

( * ) Notice: Subject to any disclaimer, the term of this patent is extended or adjusted under 35 U.S.C. 154(b) by 819 days.

(21) Appl. No.: 17/922,122

(22) PCT Filed: Apr. 26, 2021

(86) PCT No.: PCT/CN2021/089837
§ 371 (c)(1),
(2) Date: Oct. 28, 2022

(87) PCT Pub. No.: WO2021/218895
PCT Pub. Date: Nov. 4, 2021

(65) Prior Publication Data
US 2023/0235057 A1     Jul. 27, 2023

(30) Foreign Application Priority Data
Apr. 29, 2020    (CN) .......................... 202010359751.8

(51) Int. Cl.
*C07K 14/71* (2006.01)
*A61P 35/00* (2006.01)
(Continued)

(52) U.S. Cl.
CPC .......... *C07K 16/2818* (2013.01); *A61P 35/00* (2018.01); *C07K 14/70578* (2013.01);
(Continued)

(58) Field of Classification Search
None
See application file for complete search history.

(56) References Cited

U.S. PATENT DOCUMENTS 10,167,334 B2 *  1/2019  Mirza ...................... A61P 43/00
10,689,439 B2 *  6/2020  Watkins ................. C07K 16/24
(Continued)

FOREIGN PATENT DOCUMENTS

CN          106967172 A  *  7/2017  ............. C07K 16/46
CN          110734498 A     1/2020
(Continued)

OTHER PUBLICATIONS

Brorson et al., Therapeutic monoclonal antibodies and consistent ends_terminal heterogeneity, detection, and impact on quality, Curr. Opin. Biotechnol. 30:140-145, 2014.*
(Continued)

*Primary Examiner* — Claire Kaufman
(74) *Attorney, Agent, or Firm* — Kilpatrick Townsend & Stockton LLP

(57) ABSTRACT

Provided in the present disclosure are a bifunctional protein which can bind to PD-1 (programmed death receptor-1) and TGF-β (transforming growth factor-β), the medical use of the bifunctional protein, and a preparation method therefor.

3 Claims, 2 Drawing Sheets

Specification includes a Sequence Listing.

Anti-PD-1 antibody (G4S)₄G linker peptide

Extracellular domain of TGFβ RII

(51) Int. Cl.

| | | |
|---|---|---|
| *C07K 14/705* | (2006.01) | |
| *C07K 16/28* | (2006.01) | |
| *C07K 16/46* | (2006.01) | |
| *A61K 39/00* | (2006.01) | |

(52) U.S. Cl.
CPC ........ *C07K 14/71* (2013.01); *A61K 2039/505* (2013.01); *C07K 2317/565* (2013.01); *C07K 2319/30* (2013.01)

(56) References Cited

U.S. PATENT DOCUMENTS

| | | | | |
|---|---|---|---|---|
| 10,851,157 | B2 * | 12/2020 | Karow | C07K 16/2827 |
| 11,274,142 | B2 * | 3/2022 | Gu | C07K 16/32 |
| 2015/0225483 | A1 * | 8/2015 | Lo | A61P 1/18 |
| | | | | 435/69.6 |
| 2019/0185569 | A1 * | 6/2019 | Li | G01N 33/68 |
| 2019/0321466 | A1 | 10/2019 | Li et al. | |
| 2020/0002439 | A1 | 1/2020 | Sheng et al. | |
| 2020/0048351 | A1 | 2/2020 | Sabzevari et al. | |
| 2021/0115142 | A1 * | 4/2021 | Kang | A61K 31/713 |
| 2021/0246208 | A1 | 8/2021 | Lan et al. | |

FOREIGN PATENT DOCUMENTS

| | | | | |
|---|---|---|---|---|
| JP | 2019-533475 | A | 11/2019 | |
| WO | 2015/118175 | A2 | 8/2015 | |
| WO | 2018/045110 | A1 | 3/2018 | |
| WO | 2018/218215 | A1 | 11/2018 | |
| WO | WO-2018205985 | A1 * | 11/2018 | A61P 35/00 |
| WO | 2019/211489 | A1 | 11/2019 | |
| WO | 2020/014285 | A2 | 1/2020 | |
| WO | 2020/043184 | A1 | 3/2020 | |

OTHER PUBLICATIONS

Wang et al., Human IgG Subclasses Differ in the Structural Elements of Their N-Glycosylation, ACSCent. Sci. 10,2048-2058 and Suppl. Material, 2024.*
Lee et al., Molecular Interactions of Antibody Drugs Targeting PD-1, PD-L1, and CTLA-4 in Immuno-Oncology, Molecules, 24:1190, 16 pages, 2019.*
Lai et al., Differences in human IgG1 and IgG4 S228P monoclonal antibodies viscosity and self-interactions Experimental assessment and computational predictions , mAs, 13:1: e1991256, 19 pages, 2021.*
C. David et al.; TGF-β Tumor Suppression Through a Lethal EMT; Cell 164, 2016; 1015-1030.
Y. Shen et al.; TGF-β Regulates Hepatocellular Carcinoma Progression by Inducing Treg Cell Polarization; Cellular Physiology and Biochemistry; 2015; 35:1623-1632.
ISA/CN; International Search Report; PCT/CN2021/089837; mailed Jul. 29, 2021; 10 pgs.
European Patent Application No. 21795280.3, Extended European Search Report, Apr. 30, 2024, 7 pages.
Acchione, Mauro et al., "Impact of linker and conjugation chemistry on antigen binding, Fc receptor binding and thermal stability of model antibody-drug conjugates," Landes Bioscience, vol. 4, No. 3, May/Jun. 2012, pp. 362-372.
Badri, H. et al., "Optimization of radiation dosing schedules for proneural glioblastoma," J. Math. Biol., Jun. 2015, pp. 1-36.
Baylot, Virginie et al., "TCTP Has a Crucial Role in the Different Stages of Prostate Cancer Malignant Progression," Springer International Publishing AG 2017, pp. 255-261.
Kontermann, Roland E. et al., "Bispecific antibodies," Drug Discovery Today, vol. 20, No. 7, Jul. 2015, pp. 838-847.
Muller, Sylviane et al., "Spliceosomal Peptide P140 for Immunotherapy of Systemic Lupus Erythematosus," Arthritis & Rheumatism, vol. 58, No. 12, Dec. 2008, pp. 3873-3883.
Torres, Marcela et al., "The immunoglobulin constant region contributes to affinity and specificity," Trends in Immunology, vol. 29, No. 2, Feb. 2008, pp. 91-97.

* cited by examiner

Anti-PD-1 antibody (G4S)₄G linker peptide

Extracellular domain of TGFβ RII

BIFUNCTIONAL PROTEIN AGAINST PD-1 AND TGF-β

CROSS-REFERENCE TO RELATED APPLICATIONS

The present application is a § 371 National Phase Application of PCT/CN2021/089837, filed Apr. 26, 2021, which application claims priority to Chinese Patent Application No. 202010359751.8 filed on Apr. 29, 2020, the disclosure of each of which is incorporated herein by reference in its entirety and for all purposes.

INCORPORATION-BY-REFERENCE OF SEQUENCE LISTING

A Sequence Listing conforming to the rules of WIPO Standard ST.25 is hereby incorporated by reference. Said Sequence Listing has been filed as an electronic document via ASCII text. The electronic document, created on Jan. 10, 2023, is entitled "093031-1355372-005900US_ST25.txt" and is 40,048 bytes in size.

TECHNICAL FIELD

The present disclosure generally relates to the field of antibody drugs, and in particular to the treatment of malignant tumors. Specifically, the present disclosure provides a bifunctional protein which can bind to PD-1 (programmed death receptor-1) and TGF-β (transforming growth factor-β), and medical use of the bifunctional protein.

BACKGROUND

T cells express many important membrane protein immune molecules, in which PD-1 (Programmed Death-1, programmed death receptor-1, also known as CD279) protein belongs to the CD28 family of the immunoglobulin superfamily, and its ligands (PD-L1, PD-L2) belong to the B7 family. PD-L1 negatively regulates T cell immune function after binding to PD-1, and is an important peripheral T-cell inhibitory immune checkpoint. Low expression of PD-L1 in normal human tissue can maintain immune tolerance and avoid autoimmune reaction. However, tumor cells inhibit T cell immune function by high expression of PD-L1 (or release of PD-L1 soluble variant and exosome), thereby forming an immune-inhibitory tumor immune microenvironment. The T cell immune function can be restored by blocking a PD-1/PD-L1 signaling pathway, so that tumor cells can be recognized and killed. TGF-β (transforming growth factor-β) is a class of cytokines with multifunctional biological activity that can regulate physiological processes of the body by regulating proliferation, differentiation, apoptosis, adhesion, invasion and microenvironment of cells. In a typical TGF-β signaling pathway, TGF-β firstly binds to TGF-β receptor type II (TGF-βRII) and then forms a complex with TGF-β receptor type I (TGFβRI) to activate TGFβRI, the TGFβRI phosphorylates and activates R-Smad members (Smad 1, 2, 3, 5, 8), and the R-Smad then binds to Co-Smad (Smad 4) to form a complex and translocates into the nucleus to regulate transcription of target genes.

In a tumor microenvironment, high expression of TGF-β tends to be associated with invasion, metastasis, immune escape, treatment resistance and poorer prognosis (David Charles J et al., TGF-β Tumor Suppression through a Lethal EMT. [J]. *Cell,* 2016, 164(5)). Studies also have shown that TGF-β is likely to disrupt the tumor microenvironment by inducing Treg cells and inhibiting effector T cells, thereby accelerating tumor progression (Shen Yinan et al., TGF-β regulates hepatocellular carcinoma progression by inducing Treg cell polarization. [J]. *Cellular physiology and biochemistry,* 2015, 35(4)). It is also believed by scholars that TGF-β signaling is responsible for the development of anti-PD-(L)1 drug resistance in patients.

At present, studies using TGF-β and PD-1/PD-L1 as a combined target have been reported, However, further studies are urgently needed since this study direction has good prospects.

SUMMARY

In a first aspect, the present disclosure provides a bifunctional protein comprising a PD-1 (programmed death receptor-1) binding moiety and a TGF-β (transforming growth factor-β) binding moiety.

In some embodiments, the PD-1 binding moiety is an anti-PD-1 antibody or an antigen-binding fragment thereof. In some embodiments, the PD-1 binding moiety is a full-length antibody, an Fab fragment, an $F(ab')_2$ fragment, an Fv fragment or a single chain Fv fragment (scFv) against PD-1.

In some embodiments, the anti-PD-1 antibody or the antigen-binding fragment comprises a heavy chain variable region and a light chain variable region, wherein the heavy chain variable region comprises an HCDR1 having the amino acid sequence of GFAFSSYD (SEQ ID NO: 1), an HCDR2 having the amino acid sequence of ISGGGRYT (SEQ ID NO: 2) and an HCDR3 having the amino acid sequence of ANRYGEAWFAY (SEQ ID NO: 3), and the light chain variable region comprises an LCDR1 having the amino acid sequence of QDINTY (SEQ ID NO: 4), an LCDR2 having the amino acid sequence of RAN (SEQ ID NO: 5) and an LCDR3 having the amino acid sequence of LQYDEFPLT (SEQ ID NO: 6). In some embodiments, the amino acid sequence of the heavy chain variable region is set forth in SEQ ID NO: 7, and/or the amino acid sequence of the light chain variable region is set forth in SEQ ID NO: 8. In some embodiments, the anti-PD-1 antibody or the antigen-binding fragment further comprises a heavy chain constant region and a light chain constant region, wherein the amino acid sequence of the heavy chain constant region is set forth in SEQ ID NO: 9 or is a variant of the amino acid sequence set forth in SEQ ID NO: 9, for example, the amino acid sequence set forth in SEQ ID NO: 9 where residue A at the C terminus is replaced with K, and/or the amino acid sequence of the light chain constant region is set forth in SEQ ID NO: 10 or is a variant of the amino acid sequence set forth in SEQ ID NO: 10.

In other embodiments, the anti-PD-1 antibody or the antigen-binding fragment is selected from: Nivolumab, Pembrolizumab, Durvalumab, Toripalimab (JS-001), Sintilimab (IBI308), Camrelizumab, Tislelizumab (BGB-A317), AK105 (Akeso Bioscience), Genolimzumab (GB226), Livzon Mabpharm (LZM009), HLX-10, BAT-1306, AK103 (HX008), AK104 (Akeso Bioscience), CS1003, SCT-110A, F520, SG001, GLS-010, or antigen-binding fragments thereof.

In some embodiments, the TGF-β binding moiety is a TGF-β receptor or a binding domain of a TGF-β receptor. In some embodiments, the TGF-β binding moiety is an extracellular domain of a TGF-β receptor or a binding fragment of an extracellular domain of a TGF-β receptor. In some specific embodiments, the TGF-β binding moiety is a human TGF-βRII isoform B extracellular domain polypeptide comprising the amino acid sequence set forth in SEQ ID NO: 11.

In some specific embodiments, the TGF-β binding moiety is a variant of a human TGF-βRII isoform B extracellular domain polypeptide, for example, a polypeptide or peptide fragment having at least 80%, 81%, 82%, 83%, 84%, 85%, 86%, 87%, 88%, 89%, 90%, 91%, 92%, 93%, 94%, 95%, 96%, 97%, 98%, 99% or 100% identity to the amino acid sequence set forth in SEQ ID NO: 11, or any fragment described herein.

In some embodiments, the TGF-β binding moiety is an anti-TGF-β antibody or an antigen-binding fragment thereof. In some embodiments, the TGF-β binding moiety is a full-length antibody, an Fab fragment, an F(ab')₂ fragment, an Fv fragment or a single chain Fv fragment (scFv) against TGF-β.

In some embodiments, the PD-1 binding moiety and the TGF-β binding moiety are linked by a flexible linker. In some embodiments, the flexible linker is a GGGS-type linker (amino acids 2-5 of SEQ ID NO: 12). In some specific embodiments, the flexible linker is a linker set forth in SEQ ID NO: 12.

In some embodiments, the bifunctional protein comprises: (1) two identical first polypeptides, the amino acid sequence of the first polypeptide having at least 80% identity to the amino acid sequence set forth in SEQ ID NO: 13; and (2) two identical second polypeptides, the amino acid sequence of the second polypeptide having at least 80% identical to the amino acid sequence set forth in SEQ ID NO: 14.

In a second aspect, the present disclosure provides a nucleic acid molecule encoding the bifunctional protein according to the first aspect.

In a third aspect, the present disclosure provides a pharmaceutical composition comprising the bifunctional protein according to the first aspect, and a pharmaceutically acceptable excipient, diluent or carrier.

In some embodiments, the pharmaceutical composition is used for preventing or treating a malignant tumor. In some specific embodiments, the malignant tumor is selected from colorectal cancer, breast cancer, ovarian cancer, pancreatic cancer, gastric cancer, prostate cancer, renal cancer, cervical cancer, myeloma, lymphoma, leukemia, thyroid cancer, endometrial cancer, uterine cancer, bladder cancer, neuroendocrine malignant tumor, head and neck cancer, liver cancer, nasopharyngeal cancer, testicular cancer, small cell lung cancer, non-small cell lung cancer, melanoma, basal cell skin cancer, squamous cell skin cancer, dermatofibrosarcoma protuberans, Merkel cell carcinoma, glioblastoma, glioma, sarcoma, mesothelioma and/or myelodysplastic syndromes. In some specific embodiments, the malignant tumor is primary, metastatic, recurrent and/or refractory.

In a fourth aspect, the present disclosure provides use of the bifunctional protein according to the first aspect or the nucleic acid molecule according to the second aspect for preparing a medicament for preventing or treating a malignant tumor.

In some embodiments, the malignant tumor is selected from colorectal cancer, breast cancer, ovarian cancer, pancreatic cancer, gastric cancer, prostate cancer, renal cancer, cervical cancer, myeloma, lymphoma, leukemia, thyroid cancer, endometrial cancer, uterine cancer, bladder cancer, neuroendocrine malignant tumor, head and neck cancer, liver cancer, nasopharyngeal cancer, testicular cancer, small cell lung cancer, non-small cell lung cancer, melanoma, basal cell skin cancer, squamous cell skin cancer, dermatofibrosarcoma protuberans, Merkel cell carcinoma, glioblastoma, glioma, sarcoma, mesothelioma and/or myelodysplastic syndromes. In some specific embodiments, the malignant tumor is primary, metastatic, recurrent and/or refractory.

In a fifth aspect, the present disclosure provides a method for preventing or treating a malignant tumor, comprising administering the bifunctional protein according to the first aspect or the pharmaceutical composition according to the third aspect to a subject having the malignant tumor.

In some embodiments, the malignant tumor is selected from colorectal cancer, breast cancer, ovarian cancer, pancreatic cancer, gastric cancer, prostate cancer, renal cancer, cervical cancer, myeloma, lymphoma, leukemia, thyroid cancer, endometrial cancer, uterine cancer, bladder cancer, neuroendocrine malignant tumor, head and neck cancer, liver cancer, nasopharyngeal cancer, testicular cancer, small cell lung cancer, non-small cell lung cancer, melanoma, basal cell skin cancer, squamous cell skin cancer, dermatofibrosarcoma protuberans, Merkel cell carcinoma, glioblastoma, glioma, sarcoma, mesothelioma and/or myelodysplastic syndromes. In some specific embodiments, the malignant tumor is primary, metastatic, recurrent and/or refractory.

In a sixth aspect, the present disclosure provides a method for preparing a bifunctional protein comprising a PD-1 (programmed death receptor-1) binding moiety and a TGF-β (transforming growth factor-β) binding moiety and comprising the bifunctional protein according to the first aspect, wherein the method comprises the following steps:

introducing an expression vector comprising a nucleic acid molecule encoding the bifunctional protein into a host cell and culturing the host cell under a condition allowing protein expression; and collecting a cell culture and/or supernatant, and isolating and purifying the bifunctional protein.

DESCRIPTION OF THE SEQUENCES

Figure 1:
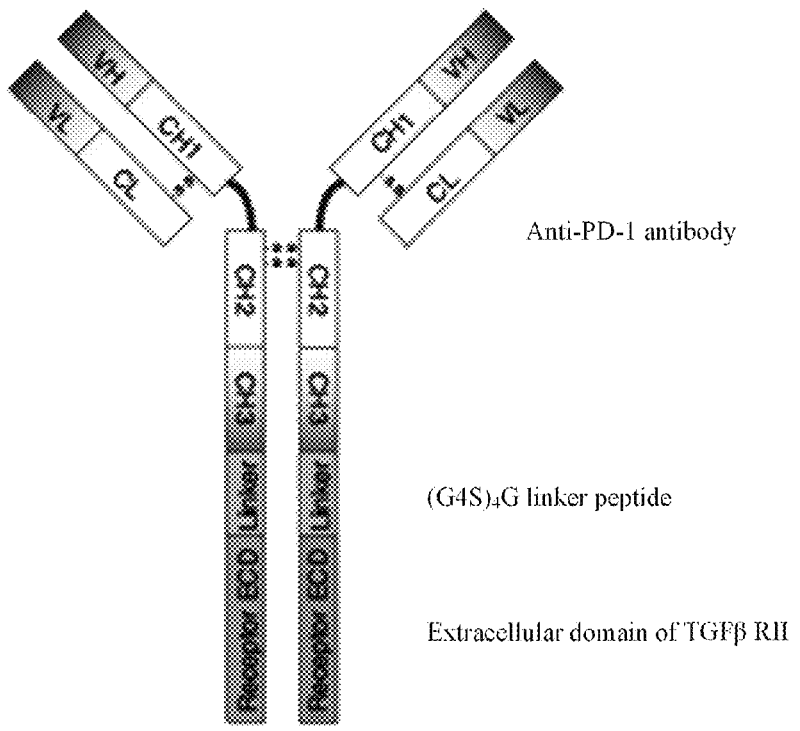
FIG. 1 shows a schematic structural diagram of an exemplary PD-1/TGFβ bifunctional protein according to the present disclosure.

SEQ ID NOs: 1 to 3 are sequences of CDR1 to CDR3 of a heavy chain variable region of an anti-PD-1 antibody portion of an exemplary PD-1/TGFβ bifunctional protein according to the present disclosure.

SEQ ID NOs: 4 to 6 are sequences of CDR1 to CDR3 of a light chain variable region of an anti-PD-1 antibody portion of an exemplary PD-1/TGFβ bifunctional protein according to the present disclosure.

SEQ ID NOs: 7 and 8 are sequences of a heavy chain variable region and a light chain variable region of an anti-PD-1 antibody portion of an exemplary PD-1/TGFβ bifunctional protein, respectively, according to the present disclosure.

SEQ ID NOs: 9 and 10 are sequences of a heavy chain constant region and a light chain constant region of an anti-PD-1 antibody portion of an exemplary PD-1/TGFβ bifunctional protein, respectively, according to the present disclosure.

SEQ ID NO: 11 is a TGF-β binding moiety of an exemplary PD-1/TGFβ bifunctional protein according to the present disclosure, i.e., a human TGF-βRII isoform B extracellular domain polypeptide.

SEQ ID NO: 12 is a flexible linker between an anti-PD-1 antibody portion and a TGF-β binding moiety of an exemplary PD-1/TGFβ bifunctional protein according to the present disclosure.

SEQ ID NO: 13 is a sequence of a heavy chain portion of an exemplary PD-1/TGFβ bifunctional protein according to the present disclosure, wherein the heavy chain portion consists of a heavy chain of an anti-PD-1 antibody portion, a flexible linker (SEQ ID NO: 12) and a human TGF-βRII isoform B extracellular domain polypeptide (SEQ ID NO: 11).

SEQ ID NO: 14 is a sequence of a light chain portion of an exemplary PD-1/TGFβ bifunctional protein according to the present disclosure, wherein the light chain portion consists of a light chain of an anti-PD-1 antibody portion.

SEQ ID NO: 15 is a nucleic acid sequence encoding SEQ ID NO: 13 (which does not comprise a coding sequence of a signal peptide).

SEQ ID NO: 16 is a nucleic acid sequence encoding SEQ ID NO: 14 (which does not comprise a coding sequence of a signal peptide).

SEQ ID NOs: 17 and 18 are sequences of a heavy chain and a light chain of control PD1 monoclonal antibody Nivolumab, respectively.

SEQ ID NOs: 19 and 14 are sequences of a heavy chain and a light chain of another control PD1 monoclonal antibody (from Chinese Patent Application No. 201610705763.5 (CN106977602)), respectively.

SEQ ID NOs: 20 and 18 are sequences of a heavy chain portion and a light chain portion of Nivolumab/TGF-βRII bifunctional protein as a bifunctional protein control, respectively, wherein the heavy chain portion consists of a heavy chain of Nivolumab (the amino acid residue at the C terminus of SEQ ID NO: 17 is mutated from K to A), a flexible linker (SEQ ID NO: 12) and a human TGF-βRII isoform B extracellular domain polypeptide (SEQ ID NO: 11), and a light chain portion consists of a light chain of Nivolumab.

SEQ ID NOs: 21 and 22 are sequences of a heavy chain and a light chain of the experimental control IgG1 protein.

DETAILED DESCRIPTION

Definitions

The following definitions and methods are provided to better define the present disclosure and to guide those of ordinary skill in the art in the practice of the present disclosure. Unless otherwise indicated, terms used in the present disclosure have meanings commonly understood by those skilled in the art. All patent documents, academic papers, and other publications cited herein are incorporated by reference in their entirety.

The term "antibody" as used herein refers to an immunoglobulin molecule that can specifically bind to a target via at least one antigen recognition site located in a variable region of the immunoglobulin molecule. The target includes, but is not limited to, a carbohydrate, a polynucleotide, a lipid, a polypeptide and the like. The "antibody" as used herein includes not only an intact (i.e., full-length) antibody, but also an antigen-binding fragment thereof (e.g., Fab, Fab', F(ab')$_2$, Fv), a variant thereof, a fusion protein comprising an antibody portion, a humanized antibody, a chimeric antibody, a diabody, a linear antibody, a single chain antibody, a multispecific antibody (e.g., a bispecific antibody), and any other modified configuration of an immunoglobulin molecule comprising an antigen recognition site of the desired specificity, including a glycosylated variant of an antibody, an amino acid sequence variant of an antibody and a covalently modified antibody.

An intact or full-length antibody generally comprises two heavy chains and two light chains. Each heavy chain comprises a heavy chain variable region (VH) and first, second and third constant regions (CH1, CH2 and CH3). Each light chain comprises a light chain variable region (VL) and a constant region (CL). The full-length antibody may be any type of antibody, such as IgD, IgE, IgG, IgA or IgM (or a subclass thereof), but the antibody needs not belong to any particular class. Immunoglobulins can be divided into different classes depending on antibody amino acid sequences of constant regions of a heavy chain. Generally, there are five main classes of immunoglobulins: IgA, IgD, IgE, IgG and IgM, and several of these classes can be further classified into subclasses (isotypes), such as IgG1, IgG2, IgG3, IgG4, IgA1 and IgA2. The heavy chain constant domains corresponding to different classes of immunoglobulins are referred to as $\alpha$, $\delta$, $\epsilon$, $\gamma$ and $\mu$, respectively. The subunit structures and three-dimensional structures of different classes of immunoglobulins are well known.

The term "antigen-binding fragment" as used herein refers to a portion of an antibody structure that determines the antigen-binding capacity. It will be appreciated by those skilled in the art that the major portion of the antibody structure that determines the antigen-binding capacity is CDR which is thus also the core component of the antigen-binding fragment. The antigen-binding domain may comprise a heavy chain variable region (VH), a light chain variable region (VL) or both the two. Each of VH and VL generally comprises three complementarity determining regions CDR1, CDR2 and CDR3.

It is well known to those skilled in the art that the complementarity determining regions (CDRs, generally CDR1, CDR2 and CDR3) are regions in a variable region that have the greatest impact on the affinity and specificity of an antibody. There are two common definitions for CDR sequences in the VH or VL, namely the Chothia definition and the Kabat definition. (see, e.g., Kabat, *Sequences of Proteins of Immunological Interest*, National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989)). For variable region sequences of a given antibody, CDR sequences in the VH and VL sequences can be determined according to the Chothia definition or the Kabat definition.

For variable region sequences of a given antibody, CDR sequences in the variable region sequence can be analyzed in a variety of ways, e.g., can be determined using the online software Abysis (www.abysis.org/).

Examples of the antigen-binding fragment include, but are not limited to: (1) an Fab fragment, which may be a monovalent fragment having a VL-CL chain and a VH-CH1 chain; (2) an F(ab')$_2$ fragment, which may be a bivalent fragment having two Fab' fragments connected by a disulfide bridge (e.g., a dimer of the Fab') in the hinge region; (3) an Fv fragment having VL and VH domains of a single arm of an antibody; (4) a single chain Fv (scFv), which may be a single polypeptide chain consisting of a VH domain and a VL domain via a peptide linker; and (5) (scFv)$_2$, which may comprise two VH domains linked by a peptide linker and two VL domains combined with the two VH domains via a disulfide bridge.

The terms "Fab fragment", "Fab portion" or similar terms as used herein refer to an antibody fragment that can bind to an antigen and that is produced by treating an intact antibody with a protease papain, including an intact light chain (VL-CL), a variable region of a heavy chain, and a CH1 fragment (VH-CH1).

The term "single chain fragment variable (scfv)" as used herein refers to an antibody with a single chain structure generally constructed by genetic engineering techniques, including one polypeptide chain of a heavy chain variable region (VH) and a light chain variable region (VL). A flexible linker peptide is generally designed between a heavy chain variable region and a light chain variable region so that the heavy chain variable region and the light chain variable region can be folded into the correct conformation that can bind to an antigen.

The terms "Fc fragment", "Fc domain", "Fc portion" or similar terms as used herein refer to a portion of a heavy chain constant region of an antibody, including a hinge region, and CH2 and CH3 fragments of the constant region.

The term "specific binding" as used herein refers to a non-random binding reaction between two molecules, such as the binding of an antibody to an antigen epitope.

The term "monoclonal antibody" as used herein refers to an antibody obtained from a substantially homogeneous population of antibodies, i.e., the individual antibodies making up the population are identical except for naturally occurring mutations that may be present in a small number of individuals. The monoclonal antibody described herein specifically includes a "chimeric" antibody in which a portion of a heavy chain and/or a light chain is identical to or homologous to corresponding sequences in an antibody derived from a particular species or belonging to a particular antibody class or subclass, while the remainder of the heavy chain and/or light chain is identical to or homologous to corresponding sequences in the antibody derived from another species or belonging to another antibody class or subclass, and also include fragments of such antibodies, so long as they exhibit the desired biological activity.

The term "identity" as used herein refers to sequence similarity between two polynucleotide sequences or between two polypeptide sequences. Sequence comparison and percent identity determination between two sequences can be performed by default settings for the BLASTN/BLASTP algorithm available on the website of national center for biotechnology institute.

The term "treating" as used herein includes therapeutic treatment and prophylactic treatment or preventative measures, in which a therapeutic agent is administered to the subject to reduce at least one symptom of a disease, disorder, or condition (e.g., cancer or tumor), or to relieve the development of symptoms.

The term "EC$_{50}$", also known as a median effective concentration, as used herein, refers to a concentration that achieves 50% of the maximum effect after a specified exposure time.

In a first aspect, the present disclosure provides a bifunctional protein comprising a PD-1 (programmed death receptor-1) binding moiety and a TGF-β (transforming growth factor-β) binding moiety.

In some embodiments, the PD-1 binding moiety is an anti-PD-1 antibody or an antigen-binding fragment thereof. In some embodiments, the PD-1 binding moiety is a full-length antibody, an Fab fragment, an F(ab')$_2$ fragment, an Fv fragment or a single chain Fv fragment (scFv) against PD-1.

In some embodiments, the anti-PD-1 antibody or the antigen-binding fragment comprises a heavy chain variable region and a light chain variable region, wherein the heavy chain variable region comprises an HCDR1 having the amino acid sequence of GFAFSSYD (SEQ ID NO: 1), an HCDR2 having the amino acid sequence of ISGGGRYT (SEQ ID NO: 2) and an HCDR3 having the amino acid sequence of ANRYGEAWFAY (SEQ ID NO: 3), and the light chain variable region comprises an LCDR1 having the amino acid sequence of QDINTY (SEQ ID NO: 4), an LCDR2 having the amino acid sequence of RAN (SEQ ID NO: 5) and an LCDR3 having the amino acid sequence of LQYDEFPLT (SEQ ID NO: 6). In some embodiments, the amino acid sequence of the heavy chain variable region is set forth in SEQ ID NO: 7, and/or the amino acid sequence of the light chain variable region is set forth in SEQ ID NO: 8. In some embodiments, the anti-PD-1 antibody or the antigen-binding fragment further comprises a heavy chain constant region and a light chain constant region, wherein the amino acid sequence of the heavy chain constant region is set forth in SEQ ID NO: 9, and/or the amino acid sequence of the light chain constant region is set forth in SEQ ID NO: 10.

In some embodiments, the amino acid sequence of the heavy chain constant region is a variant of SEQ ID NO: 9, and/or the amino acid sequence of the light chain constant region is a variant of SEQ ID NO: 10. In some specific embodiments, the amino acid sequence of the heavy chain constant region is the amino acid sequence set forth in SEQ ID NO: 9 where residue A at the C terminus is replaced with K. Modifications to an antibody constant region are known to those skilled in the art. In some embodiments, the heavy chain constant region may be selected from IgG1, IgG2, IgG3, IgG4, or other classes, although IgG1 is preferred. In some embodiments, the antibody constant region may comprise modifications, e.g., insertions, deletions, substitutions or chemical modifications to amino acids. In some embodiments, any amino acid residue of the constant region may be substituted by an amino acid residue of any allotype, preferably by an amino acid residue of G1m(3) and/or nG1m(1). In some embodiments, the constant region comprises a mutation that alters effector function. For example, a lysine residue (K) at the C terminus of the antibody heavy chain constant region (commonly found in wild-type IgG1 antibodies) is mutated to a hydrophobic amino acid, such as alanine (A) or leucine (L), thereby reducing hydrolytic cleavage by proteases and prolonging the serum half-life, and this modification is also particularly suitable for the case where the C terminus of the antibody heavy chain is further fused to other portion. A residue at the C terminus of the heavy chain constant region of the anti-PD-1 antibody portion in the exemplary PD-1/TGFβ bifunctional proteins according to the present disclosure is treated accordingly.

In some embodiments, the TGF-β binding moiety is a TGF-β receptor or a binding domain of a TGF-β receptor. In some embodiments, the TGF-β binding moiety is an extracellular domain of a TGF-β receptor or a binding fragment of an extracellular domain of a TGF-β receptor. In some specific embodiments, the TGF-β binding moiety is a human TGF-βRII isoform B extracellular domain polypeptide comprising the amino acid sequence set forth in SEQ ID NO: 11. In some specific embodiments, the TGF-β binding moiety is a variant of a human TGF-βRII isoform B extracellular domain polypeptide, for example, a polypeptide or peptide fragment having at least 80%, 81%, 82%, 83%, 84%, 85%, 86%, 87%, 88%, 89%, 90%, 91%, 92%, 93%, 94%, 95%, 96%, 97%, 98%, 99% or 100% identity to the amino acid sequence set forth in SEQ ID NO: 11, or any fragment described herein.

In some embodiments, the TGF-β binding moiety is an anti-TGF-β antibody or an antigen-binding fragment thereof. In some embodiments, the TGF-β binding moiety is a full-length antibody, an Fab fragment, an F(ab')₂ fragment, an Fv fragment or a single chain Fv fragment (scFv) against TGF-β.

In some embodiments, the PD-1 binding moiety and the TGF-β binding moiety are linked by a flexible linker. In some embodiments, the flexible linker is a GGGS-type linker (amino acids 2-5 of SEQ ID NO: 12). In some specific embodiments, the flexible linker is a linker set forth in SEQ ID NO: 12.

In certain embodiments, the bifunctional protein comprises: (1) two identical first polypeptides, the amino acid sequence of the first polypeptide having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identity to the amino acid sequence set forth in SEQ ID NO: 13; and (2) two identical second polypeptides, the amino acid sequence of the second polypeptide having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence set forth in SEQ ID NO: 14.

As non-limiting examples, the bifunctional protein (i.e., PD-1/TGFβ bifunctional protein, hereinafter also referred to as "PD1/TGFβRII fusion protein" or "PD1/TGFβRII") according to the present disclosure may consist of an anti-PD-1 antibody (amino acid sequences of a heavy chain variable region, a light chain variable region, a heavy chain constant region and a light chain constant region thereof are set forth in SEQ ID NOs: 7, 8, 9 and 10, respectively), a flexible linker (SEQ ID NO: 12) and a human TGF-βRII isoform B extracellular domain polypeptide (SEQ ID NO: 11), and the schematic diagram of the molecular structure of the bifunctional protein is shown in FIG. 1. As shown in FIG. 1, PD1/TGFβRII, based on a natural anti-PD-1 antibody, extends a flexible linker and a human TGF-βRII isoform B extracellular domain polypeptide in sequence at the CH3 terminus of the heavy chain constant region.

PD1/TGFβRII is an exemplary bifunctional protein according to the present disclosure, and has higher TGFβ binding activity and PD-1 binding moiety biological activity and even better tumor inhibition effect compared with the reported Nivolumab/TGF-βRII fusion protein. In addition, PD1/TGFβRII has lower cytotoxicity and side effects relative to existing anti-PD-1 antibodies, such as Nivolumab. Given existing anti-PD-1 antibodies having greater cytotoxicity and side effects, PD1/TGFβRII having lower cytotoxicity and side effects makes it possible to administer at higher doses to better inhibit and consume TGFβ with a more desirable dose safety window, and facilitates high dose administration and clinical application.

In a second aspect, the present disclosure provides a nucleic acid molecule encoding the bifunctional protein according to the first aspect.

In a third aspect, the present disclosure provides a pharmaceutical composition comprising the bifunctional protein according to the first aspect, and a pharmaceutically acceptable excipient, diluent or carrier.

In some embodiments, the pharmaceutical composition is used for preventing or treating a malignant tumor. In some specific embodiments, the malignant tumor is selected from colorectal cancer, breast cancer, ovarian cancer, pancreatic cancer, gastric cancer, prostate cancer, renal cancer, cervical cancer, myeloma, lymphoma, leukemia, thyroid cancer, endometrial cancer, uterine cancer, bladder cancer, neuroendocrine malignant tumor, head and neck cancer, liver cancer, nasopharyngeal cancer, testicular cancer, small cell lung cancer, non-small cell lung cancer, melanoma, basal cell skin cancer, squamous cell skin cancer, dermatofibrosarcoma protuberans, Merkel cell carcinoma, glioblastoma, glioma, sarcoma, mesothelioma and/or myelodysplastic syndromes. In some specific embodiments, the malignant tumor is primary, metastatic, recurrent and/or refractory.

In some embodiments, the pharmaceutical composition may further comprise a lubricant such as talc, magnesium stearate and mineral oil; a wetting agent; an emulsifier; a suspending agent; a preservative such as benzoic acid, sorbic acid and calcium propionate; a sweetener and/or a flavoring agent, and the like.

In some embodiments, the pharmaceutical composition according to the present disclosure can be formulated in the form of tablets, pills, powders, pastilles, elixirs, suspensions, emulsions, solutions, syrups, suppositories or capsules, and the like.

In some embodiments, the pharmaceutical composition according to the present disclosure may be delivered using any physiologically acceptable mode of administration, including, but not limited to: oral administration, parenteral administration, nasal administration, rectal administration, intraperitoneal administration, intravascular injection, subcutaneous administration, transdermal administration, inhalation administration, and the like.

In some embodiments, the pharmaceutical composition for therapeutic use may be formulated for storage in lyophilized formulations or aqueous solutions by mixing an agent with the desired purity with optionally pharmaceutically acceptable carriers, excipients and the like.

In a fourth aspect, the present disclosure provides use of the bifunctional protein according to the first aspect or the nucleic acid molecule according to the second aspect for preparing a medicament for preventing or treating a malignant tumor.

In some embodiments, the malignant tumor is selected from colorectal cancer, breast cancer, ovarian cancer, pancreatic cancer, gastric cancer, prostate cancer, renal cancer, cervical cancer, myeloma, lymphoma, leukemia, thyroid cancer, endometrial cancer, uterine cancer, bladder cancer, neuroendocrine malignant tumor, head and neck cancer, liver cancer, nasopharyngeal cancer, testicular cancer, small cell lung cancer, non-small cell lung cancer, melanoma, basal cell skin cancer, squamous cell skin cancer, dermatofibrosarcoma protuberans, Merkel cell carcinoma, glioblastoma, glioma, sarcoma, mesothelioma and/or myelodysplastic syndromes. In some specific embodiments, the malignant tumor is primary, metastatic, recurrent and/or refractory.

In a fifth aspect, the present disclosure provides a method for preventing or treating a malignant tumor, comprising administering the bifunctional protein according to the first aspect or the pharmaceutical composition according to the third aspect to a subject having the malignant tumor.

In some embodiments, the malignant tumor is selected from colorectal cancer, breast cancer, ovarian cancer, pancreatic cancer, gastric cancer, prostate cancer, renal cancer, cervical cancer, myeloma, lymphoma, leukemia, thyroid cancer, endometrial cancer, uterine cancer, bladder cancer, neuroendocrine malignant tumor, head and neck cancer, liver cancer, nasopharyngeal cancer, testicular cancer, small cell lung cancer, non-small cell lung cancer, melanoma, basal cell skin cancer, squamous cell skin cancer, dermato-fibrosarcoma protuberans, Merkel cell carcinoma, glioblastoma, glioma, sarcoma, mesothelioma and/or myelodysplastic syndromes. In some specific embodiments, the malignant tumor is primary, metastatic, recurrent and/or refractory.

In a sixth aspect, the present disclosure provides a method for preparing a bifunctional protein comprising a PD-1 (programmed death receptor-1) binding moiety and a TGF-β (transforming growth factor-β) binding moiety, wherein the method comprises the following steps:

introducing an expression vector comprising a nucleic acid molecule encoding the bifunctional protein into a host cell and culturing the host cell under a condition allowing protein expression; and collecting a cell culture and/or supernatant, and isolating and purifying the bifunctional protein.

Without being contradicted, the embodiments and technical features described in the first aspect also apply to the sixth aspect.

In some embodiments, the host cell is a mammalian cell, such as a CHO cell.

In some embodiments, the supernatant after centrifugation of the cell culture is collected.

In some embodiments, purifying the bifunctional protein is performed by using one or more of affinity chromatography, anion exchange chromatography and cation exchange chromatography. In some embodiments of affinity chromatography, an elution solution comprises sucrose or glycerol. The inventors of the present disclosure found that an elution solution added with sucrose or glycerol is advantageous for reducing the degradation of the fusion protein.

The following examples are for illustrative purposes only and are not intended to limit the scope of the present disclosure.

EXAMPLES

Example 1: Expression of PD1/TGFβRII Fusion Protein

In this example, PD1/TGFβRII fusion protein according to the present disclosure was constructed, and the schematic structural diagram thereof is shown in FIG. 1. The nucleotide sequence encoding a heavy chain portion (SEQ ID NO: 13) and a light chain portion (SEQ ID NO: 14) of the PD1/TGFβRII fusion protein fused with the signal peptide was synthesized and cloned into pcDNA3.1 expression vector. The expression vector of the PD1/TGFβRII fusion protein was co-transfected into CHO cells using standard protocols for transient or stable transfection, and the transfected cells were cultured in an incubator at 37° C. with 8% CO_2.

The amino acid sequence (SEQ ID NO: 11) of the human TGF-βRII isoform B extracellular domain polypeptide included in SEQ ID NO: 13:

IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD

The amino acid sequence (SEQ ID NO: 12) of the linker included in SEQ ID NO: 13:

GGGGSGGGGSGGGGSGGGGSG

12

The amino acid sequence (SEQ ID NO: 13) of the PD1/TGFβRII fusion protein heavy chain:

EVQLVESGGGLVQPGGSLRLSCAASGFAFSSYDMSWVRQAPGKGLDWVAT

ISGGGRYTYYPDSVKGRFTISRDNSKNNLYLQMNSLRAEDTALYYCANRY

GEAWFAYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPEAAGAPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGAGG

GGSGGGGSGGGGSGGGGSGIPPHVQKSVNNDMIVTDNNGAVKFPQLCKFC

DVRFSTCDNQKSCMSNCSITSICEKPQEVCVAVWRKNDENITLETVCHDP

KLPYHDFILEDAASPKCIMKEKKKPGETFFMCSCSSDECNDNIIFSEEYN

TSNPD

The amino acid sequence (SEQ ID NO: 14) of the PD1/TGFβRII fusion protein light chain:

DIQMTQSPSSMSASVGDRVTFTCRASQDINTYLSWFQQKPGKSPKTLIYR

ANRLVSGVPSRFSGSGSGQDYTLTISSLQPEDMATYYCLQYDEFPLTFGA

GTKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Example 2: Purification of PD1/TGFβRII Fusion Protein

The cell culture obtained in Example 1 was centrifuged, and the supernatant was collected and subjected to the first-step purification using Protein A affinity chromatography. The equilibration buffer was 10 mmol/L phosphate buffered saline at pH 6.0. After the chromatography column was washed for 3-5 column volumes with the equilibration buffer, the cell supernatant was loaded. After the loading was completed, the chromatography column was washed with equilibration buffer. Then the chromatography column was rinsed with a rinsing buffer (0.5 mol/L sodium chloride+25 mmol/L phosphate buffered saline, pH 7.0), and then equilibrated for 3-5 column volumes with the equilibration buffer. Finally, the chromatography column was washed with an elution buffer (20 mmol/L citrate buffered saline+5% sucrose, pH 3.6), and the eluted sample was collected and neutralized with 2M Tris-HCl buffer (pH 9.5).

The above eluted sample (pH 6.0) after neutralization was subjected to anion exchange chromatography. The equilibration buffer was 10 mmol/L citrate buffered saline+10 mmol/L phosphate buffered saline+10 mmol/L Tris at pH 6.0. After the chromatography column was washed for 3 to 5 column volumes with the equilibration buffer, the above eluted sample after neutralization was loaded, the flow-through sample was collected, and the chromatography column was washed with equilibration buffer after the loading was completed.

The above flow-through sample after anion exchange chromatography was subjected to cation exchange chromatography. The equilibration buffer was 10 mmol/L citric acid+10 mmol/L sodium dihydrogen phosphate+10 mmol/L Tris buffer at pH 5.0.

The above flow-through sample after anion chromatography was adjusted to pH 5.0 and loaded, and the chromatography column was washed for 3 to 5 column volumes with the equilibration buffer after the loading was completed. Then the chromatography column was eluted with an elution buffer (10 mmol/L citrate+10 mmol/L phosphate+10 mmol/L Tris buffer, pH 9.0), and the eluate was collected.

Example 3: Detection of PD1/TGFβRII Fusion Protein Sample by Size Exclusion Chromatography The components of the purified PD1/TGFβRII fusion protein sample in Example 2 were separated using a gel column chromatography. Elution was performed using a neutral buffer as the mobile phase, and the components with different molecular weights were eluted out in descending order according to their molecular weights. The gel chromatography column used was an Thermo MabPac™ SEC-1 300 Å, 5 μm, 7.8×300 mm with mobile phase (20 mmol/L disodium hydrogen phosphate+300 mmol/L sodium chloride+2% isopropanol solution, pH=7.4). The sample was diluted with the mobile phase to obtain a 1 mg/mL test solution, 50 μL of which was precisely measured out and injected into a liquid chromatography for detection at 280 nm wavelength. The flow rate was at 0.5 mL/min, and isocratic elution was performed for 35 min.

The results were quantitatively analyzed using the area normalization method. The peak area percentages of the high molecular weight impurities, immunoglobulin monomers and low molecular weight impurities were calculated. After detection, the peak area percentage of the high molecular weight impurities in the PD1/TGFβRII fusion protein sample was 0.19%, the peak area percentage of the immunoglobulin monomers therein was 99.81%, and the low molecular weight impurities were undetectable.

The control bifunctional protein (Nivolumab/TGF-βRII fusion protein) used in the following examples was prepared according to the same process, wherein the amino acid residue at the C terminus of the original heavy chain constant region of Nivolumab was changed from K to A, and the control bifunctional protein was consistent with the exemplary PD1/TGFβRII fusion protein according to the present disclosure.

Example 4: PD-1 Binding Moiety Biological Activity of PD1/TGFβRII Fusion Protein by Reporter Gene Assay The assay process was described as follows: CHO-PDL1-CD3L cells (purchased from National Institutes for Food and Drug Control) in the logarithmic growth phase were taken, and the viable cell density was adjusted to $5\times10^5$ cells/mL by using a DMED/F12 complete medium. The cells were added into a 96-well all-white plate at 100 μL/well, and the plate was incubated in a cell incubator with 5% $CO_2$ at 37° C. for 16 to 20 h. A suspension of Jurkat-PD-1-NFAT cells (purchased from National Institutes for Food and Drug Control) was prepared the next day, and the viable cell density was adjusted to $2\times10^6$ cells/mL by using 1640 basic medium containing 2% FBS. The 96-well all-white plate to which CHO-PDL1-CD3L cells were added was taken out of the incubator, the supernatant was discarded, and the plate was added with Jurkat-PD-1-NFAT cell suspension at 50 μL/well. Then serial dilutions (with an initial concentration of 200,000 ng/mL, 3-fold serially diluted, 11 dilutions in total) of a control anti-PD-1 antibody (Nivolumab, the amino acid sequences of the heavy chain and the light chain are set forth in SEQ ID NOs: 17 and 18, respectively) or that of the PD1/TGFβRII fusion protein prepared in Examples 1 to 3 according to the present disclosure were added at 50 μL/well to the above 96-well all-white plate, and the plate was incubated in a cell incubator with 5% $CO_2$ at 37° C. for 4 to 6 h. During the incubation, the Bio-Lite luciferase reagent (Vazyme, DD1201-03) was taken out, melted at room temperature, and added into the above 96-well all-white plate at 100 μL/well after the incubation was completed. The plate was incubated in the dark at room temperature for 2 to 3 min, and the RLU value was read using a multi-functional microplate reader (Thermo, Varioskan Flash). The experimental data were analyzed using Prism software, the dose-response curves of the control and the test sample were drawn to obtain the $EC_{50}$ values of the control and the test sample, and the biological activity of the test sample was calculated.

$$\text{Biological activity (\%) of test sample} = (EC_{50} \text{ value of control}/EC_{50} \text{ value of test sample}) \times 100\%$$

Figure 2:
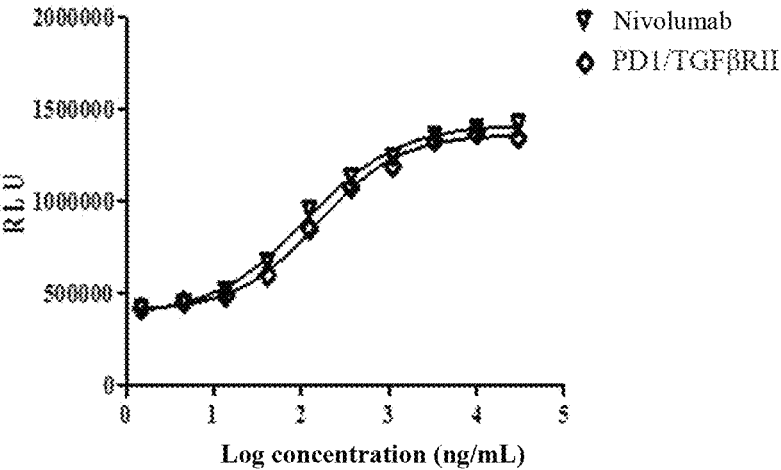
FIG. 2 shows the results of a reporter gene assay for the biological activity of the PD-1 binding moiety of an exemplary PD-1/TGFβ bifunctional protein according to the present disclosure, wherein Nivolumab is used as a control sample.

The results of the PD-1 binding moiety biological activity of the PD1/TGFβRII fusion protein in the examples according to the present disclosure are shown in Table 1 and FIG. 2, and the results show that the fusion protein retains the binding ability to human PD-1.

TABLE 1

PD-1 binding moiety biological activity of PD1/TGFβRII fusion protein

| Sample | $EC_{50}$ value (ng/mL) | Biological activity |
|---|---|---|
| Nivolumab | 113.7 | 100% |
| PD1/TGFβRII | 157.8 | 72% |

Example 5: TGFβ Binding Activity of PD1/TGFβRII Fusion Protein by Enzyme-Linked Immunosorbent Assay The assay process was as follows:
1) A high-adsorption 96-well plate was coated with 2 μg/mL human TGFβ1 protein (Sinobiological, 10804-H08H) serving as an antigen at 100 μL/well, and incubated overnight at 2 to 8° C.
2) After the 96-well plate was washed 3 times with PBST20 (PBS solution containing 0.05% Tween 20) at 250 μL/well, the plate was added with a blocking solution (PBS solution containing 3% BSA) at 250 μL/well and incubated at 25° C. for 2 h.
3) After the 96-well plate was washed 3 times with PBST20 at 250 μL/well, the plate was added with the serially diluted PD1/TGFβRII fusion protein prepared in Examples 1 to 3 according to the present disclosure (with an initial concentration of 4000 ng/mL, 4-fold serially diluted, 7 dilutions in total) at 100 μL/well and incubated at 25° C. for 2 h.
6) After the 96-well plate was washed 3 times with PBST20 at 250 μL/well, each well was added with 100 μL of HRP-goat anti-human IgG antibody (PE, NEF802001EA) diluted at 1:3500 and incubated at 25° C. for 1 h.

7) After the 96-well plate was washed 5 times with PBST20 at 250 μL/well, the plate was added with TMB solution 100 μL/well and incubated at 25° C. for 5 min in the dark.

10) The reaction was terminated by adding 1 mol/L $H_2SO_4$ at 100 μL/well, and the mixture was left at room temperature for 5 min. OD values at a wavelength of 450 nm/650 nm were measured by a microplate reader (Thermo Scientific, Varioskan Flash), and data were analyzed by Graphpad Prism.

Binding activity (%) of test sample=($EC_{50}$ value of control/$EC_{50}$ value of test sample)×100%

Figure 3:
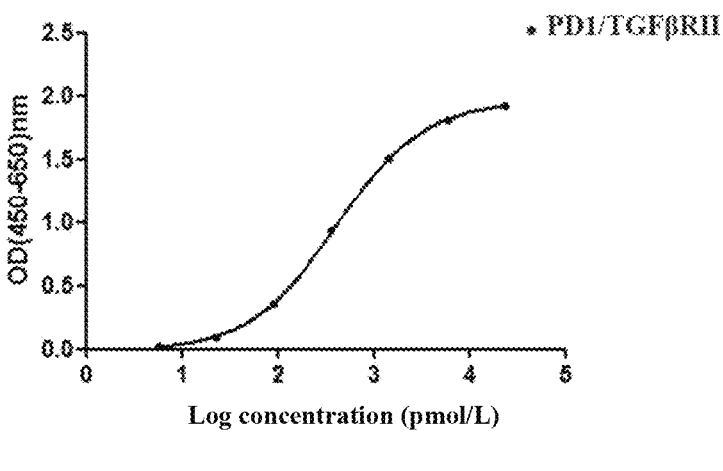
FIG. 3 shows the results of an enzyme-linked immunosorbent assay for TGF-β binding activity of an exemplary PD-1/TGFβ bifunctional protein according to the present disclosure.

The results of in vitro binding of the PD1/TGFβRII fusion protein in the examples according to the present disclosure to TGFβ1 are shown in Table 2 and FIG. 3, and the ELISA results show that the fusion protein retains the binding activity to human TGFβ.

TABLE 2

Binding activity of PD1/TGFβRII fusion protein to TGFβ

| Sample | $EC_{50}$ value (pmol/L) |
| --- | --- |
| PD1/TGFβRII | 397.6 |

Example 6: Efficacy of PD1/TGFβRII Fusion Protein on Mouse Subcutaneous Graft Tumor of Colon Cancer Cells MC38/hPD-L1

C57/PD-1 transgenic mice (purchased from Jiangsu Gem-Pharmatech Co., Ltd.) were used as experimental mice, and each mouse was subcutaneously inoculated with $3×10^5$ MC38/hPD-L1 cells. When tumors grew to 40 to 70 mm³, the mice were grouped according to tumor volume and intraperitoneally (ip) injected with drug once every 2 days for 6 times in total, and the injection volume was 0.1 mL/10 g body weight. The dosage regimen is shown in Table 3, and the day of administration was DO. The diameters of the tumors were measured twice weekly with a vernier caliper. The effect of the drug on tumor growth was examined based on the obtained T/C % or tumor growth inhibition TGI (%) calculated by the following formulas. At the end of the experiment, at the study endpoint, or when the tumor volume reached 1500 mm³, the animals were sacrificed by $CO_2$ anesthesia and dissected to take out the tumors.

The tumors were photographed.

The calculation formula of the tumor volume (V) is: $V=½×a×b^2$, wherein a and b represent the length and the width respectively; $T/C\ (\%)=(T-T_0)/(C-C_0)×100$, wherein T and C are the tumor volumes of the treated mice and the negative control mice at the end of the experiment, respectively; $T_0$ and $C_0$ are the tumor volumes of the treated mice and the negative control mice at the beginning of the experiment, respectively; and the T/C values of the treatment group and the negative control group are calculated according to the T/C values of the treated mice and the negative control mice, respectively; tumor growth inhibition (TGI) (%)=100−T/C (%). As shown in Table 4, the tumor growth inhibition rate of the PD1/TGFβRII (3.7 mg/kg, IP, twice a day, 6 times in total) prepared in Examples 1 to 3 according to the present disclosure against on subcutaneous graft tumors of MC38/hPD-L1 on D19 was 74%, which was superior to that of control anti-PD-1 monoclonal antibody; the tumor-bearing mice could tolerate the drug well and had no symptoms such as significant weight loss.

TABLE 3

Dosage regimen

| Grouping | Dose of administration (mg/kg) | Mode of administration | Volume of administration (mL/kg) | Time of administration |
| --- | --- | --- | --- | --- |
| hIgG4 | 3.7 | Intra-peritoneal | 10 | D 0, 2, 4, 6, 8, 10 |
| Control anti-PD-1 monoclonal antibody | 3 | Intra-peritoneal | 10 | D 0, 2, 4, 6, 8, 10 |
| PD1/TGFβRII fusion protein | 3.7 | Intra-peritoneal | 10 | D 0, 2, 4, 6, 8, 10 |

TABLE 4

Efficacy of PD1/TGFβRII on subcutaneous graft tumors of colon cancer cells MC38/hPD-L1

| Grouping | Mean tumor volume (mm³) | | % T/C | % TGI | Number of animals per group at the beginning of the experiment | Number of animals per group at the end of the experiment |
| --- | --- | --- | --- | --- | --- | --- |
| | D 0 | D 19 | D 19 | D 19 | | |
| hIgG4 | 55.1 ± 0.8 | 2650.9 ± 431.4 | — | — | 10 | 10 |
| Control anti-PD-1 monoclonal antibody | 53.1 ± 0.9 | 1115.2 ± 576.3 | 57 | 43 | 10 | 10 |
| PD1/TGFβRII fusion protein | 53.3 ± 0.5 | 537.0 ± 280.9 | 26 | 74 | 10 | 10 |

Note:

hIgG4 (Sino Biological Inc, HG4K) was used as a negative control. the control PD1 monoclonal antibody is antibody 14C12H1L1 described in Chinese Patent Application No. 201610705763.5 (CN106977602), and amino acid sequences of the heavy chain and the light chain are set forth in SEQ ID NOs: 19 and 14, respectively, in the present disclosure.

Example 7: In Vitro Activity Assay of PD1/TGFβRII Fusion Protein

Exemplary PD1/TGFβRII fusion protein according to the present disclosure and Nivolumab/TGF-βRII fusion protein were prepared in a batch with reference to the method of Examples 1 to 3. The PD-1 binding moiety biological activity of the PD1/TGFβRII fusion protein was assayed by the reporter gene assay with reference to Example 4 and compared with that of Nivolumab/TGF-βRII fusion protein, and the results show that: the PD-1 binding moiety biological activity of the PD1/TGFβRII fusion protein was superior to that of the Nivolumab/TGF-βRII fusion protein. The results are shown in Table 5. The TGFβ binding activity of the PD1/TGFβRII fusion protein was assayed by the an enzyme-linked immunosorbent assay with reference to Example 5 and compared with that of Nivolumab/TGF-βRII fusion protein, and the results show that: the TGFβ binding activity of the PD1/TGFβRII fusion protein was superior to that of the Nivolumab/TGF-βRII fusion protein. The results are shown in Table 6. The Nivolumab/TGF-βRII fusion protein in this example and the following examples were prepared in-house and have heavy chain and light chain sequences set forth in SEQ ID NOs: 20 and 18, respectively.

TABLE 5

| PD-1 binding moiety biological activity of PD1/TGFβRII fusion protein | | |
|---|---|---|
| Sample | EC$_{50}$ value (ng/mL) | Biological activity |
| PD1/TGFβRII | 282.4 | 100% |
| Nivolumab/TGF-βRII | 343.8 | 82% |

TABLE 6

| Binding activity of PD1/TGFβRII fusion protein to TGFP | | |
|---|---|---|
| Sample | EC$_{50}$ value (ng/mL) | Binding activity |
| Nivolumab/TGFβRII | 81.48 | 76% |
| PD1/TGFβRII | 61.74 | 100% |

Example 8: Efficacy of PD1/TGFβRII Fusion Protein on Mouse Graft Tumor of MC38/hPD-L1

Humanized PD-1 mice (purchased from Biocytogen Beijing Co., Ltd.) were used as experimental mice, and $4 \times 10^5$ MC38/hPD-L1 cells were inoculated in the right axilla of each mouse. When tumors grew to 100 to 300 mm$^3$, the mice were randomly divided into 3 groups and intraperitoneally (ip) injected with drug for 8 times in total. The dosage regimen is shown in Table 7, and the day of administration was D0. Tumor volumes were measured 2 to 3 times weekly, and mouse body weights were recorded 2 to 3 times weekly. The diameters of the tumors were measured with a vernier caliper. The effect of the drug on tumor growth was examined based on the T/C % or tumor growth inhibition (1-T/C) calculated following formulas. At the end of the experiment, the animals were sacrificed by $CO_2$ anesthesia and dissected to take out the tumors. The tumors were photographed.

The calculation formula of the tumor volume (TV) is: TV=½×a×b$^2$, wherein a and b represent the length and the width, respectively; the calculation formula of the relative tumor volume (RTV) is: RTV=(TV$_t$)/(TV$_0$), wherein TV$_0$ represents mouse tumor volume at D0, and TV$_t$ represents mouse tumor volume at each measurement; the calculation formula of the relative tumor proliferation rate T/C (e) is: T/C (%) T$_{RTV}$/C$_{RTV}$×1000, wherein T$_{RTV}$ represents RTV of treatment group, and C$_{RTV}$ represents RTV of PBS group.

The results are shown in Tables 8 and 9, and the tumor volume inhibition rates of PD1/TGFβRII and Nivolumab/TGFβRII (prepared in the same batch as shown in Example 7) on mice with MC38/hPD-L1 graft tumors on D23 were 46.8% and 32.3%, respectively, which showed that the tumor inhibition effect of PD1/TGFβRII according to the present disclosure was superior to that of Nivolumab/TGFβRII. In addition, the body weights of mice in the PD1/TGFβRII group and the Nivolumab/TGF-βRII group increased with fluctuation, indicating that neither fusion protein caused obvious toxic responses.

TABLE 7

| | | Dosage regimen | | | |
|---|---|---|---|---|---|
| Groups | Grouping | Volume of administration (mL/kg) | Time of administration, dose of administration | Number of animals per group at the beginning of the experiment | Number of animals per group at the end of the experiment |
| 1 | PBS | 10 | D 0, 3, 7, 10 (4 mg/kg per administration) D 11 (10 mg/kg per administration) D 14, 17, 21 (20 mg/kg per administration) | 8 | 8 |
| 2 | Nivolumab/ TGF-βRII | 10 | D 0, 3, 7, 10 (4 mg/kg per administration) D 11 (10 mg/kg per administration) D 14, 17, 21 (20 mg/kg per administration) | 8 | 8 |
| 3 | PD1/ TGFβRII | 10 | D 0, 3, 7, 10 (4 mg/kg per administration) D 11 (10 mg/kg per administration) D 14, 17, 21 (20 mg/kg per administration) | 8 | 8 |

TABLE 8

Effect of PD1/TGFβRII on tumor volume (TV) of mice with
MC38/hPD-L1 graft tumors

| | Tumor volume (mm³) Mean ± standard deviation | | | | | | | | |
|---|---|---|---|---|---|---|---|---|---|
| Groups | D 0 | D 3 | D 6 | D 9 | D 11 | D 14 | D 17 | D 20 | D 23 |
| 1 | 112 ± 28 | 155 ± 33 | 276 ± 90 | 393 ± 136 | 512 ± 219 | 696 ± 384 | 811 ± 441 | 1071 ± 776 | 1291 ± 965 |
| 2 | 111 ± 20 | 176 ± 57 | 268 ± 96 | 358 ± 129 | 471 ± 181 | 606 ± 238 | 689 ± 252 | 827 ± 358 | 941 ± 330 |
| 3 | 112 ± 24 | 166 ± 74 | 264 ± 106 | 327 ± 136 | 428 ± 180 | 510 ± 271 | 559 ± 324 | 670 ± 359 | 801 ± 474 |

TABLE 9

Tumor growth inhibition rate of PD1/TGFβRII on mice with
MC38/hPD-L1 graft tumors

| | T/C (%) | | | | | | | | Inhibition rate 1-T/C |
|---|---|---|---|---|---|---|---|---|---|
| Groups | D 3 | D 6 | D 9 | D 11 | D 14 | D 17 | D 20 | D 23 | D 23 |
| 1 | — | — | — | — | — | — | — | — | — |
| 2 | 110.4% | 93.3% | 86.9% | 85.9% | 80.7% | 79.7% | 70.8% | 67.7% | 32.3% |
| 3 | 100.7% | 93.3% | 80.6% | 77.8% | 66.3% | 62.4% | 54.4% | 53.2% | 46.8% |

Example 9: Stimulation of PD1/TGFβRII Fusion Protein on Cytokine Secretion Measured by Electrochemiluminescence PBMCs were adjusted with an RPMI1640 complete medium to a concentration of about $2 \times 10^6$ cells/mL, and then added to a 96-well cell culture plate at 100 μL/well. IgG1 protein (the amino acid sequences of the heavy chain and the light chain are set forth in SEQ ID NO: 21 and SEQ ID NO: 22, respectively, prepared in-house), LPS (SIGMA, L4391-1MG), and the PD1/TGFβRII fusion protein according to the present disclosure were diluted with an RPMI1640 complete medium to formulate into 900 μg/mL IgG1 protein, 1 μg/mL LPS, and 10 μg/mL, 100 μg/mL and 900 μg/mL PD1/TGFβRII fusion proteins, respectively, and RPMI1640 complete medium was used as a negative control. The solutions prepared above was added into the 96-well cell culture plate at 100 μL/well and well mixed. The plate was cultured in a cell incubator with 5% $CO_2$ at 37° C. The cell supernatant was collected from the 96-well plate at 48 h. The contents of cytokines IL-2, IL-6, IL-8, IL-10, TNF-α and IFN-γ were measured using a V-PLEX Proinflammatory Panel 1 (human) kit (MSD, K15049D-2) and measured by an ultrasensitive multifactor electrochemiluminescence analyzer (MSD, QuickPlexSQ120), and the results are shown in Table 10.

TABLE 10

Results of stimulation of test samples on cytokine secretion by
electrochemiluminescence

| Grouping | IL-2 (pg/ml) | IL-6 (pg/ml) | IL-8 (pg/ml) | IL-10 (pg/ml) | TNF-α (pg/ml) | IFN-γ (pg/ml) |
|---|---|---|---|---|---|---|
| RPMI1640 complete medium | 9.28 ± 5.14 | 2.86 ± 0.61 | 2118.44 ± 315.51 | 0.65 ± 0.32 | 2.90 ± 1.17 | 2.23 ± 0.91 |
| IgG1 protein | 13.72 ± 6.58 | 3.11 ± 0.90 | 3065.51 ± 599.37 | 0.38 ± 0.00 | 3.37 ± 0.91 | 3.42 ± 2.99 |
| LPS | 23.42 ± 2.34 | 2892.00 ± 0.00 | 9792.00 ± 0.00 | 167.79 ± 28.95 | 1456.00 ± 0.00 | 2039.78 ± 227.63 |
| PD1/TGFβRII (with a final concentration of 450 μg/mL) | 10.97 ± 1.93 | 4.02 ± 0.35 | 2613.21 ± 322.13 | 0.38 ± 0.00 | 3.15 ± 0.39 | 39.36 ± 31.46 |
| PD1/TGFβRII (with a final concentration of 50 μg/mL) | 6.59 ± 0.25 | 3.26 ± 0.37 | 2188.06 ± 474.45 | 0.47 ± 0.15 | 2.78 ± 0.42 | 14.02 ± 10.96 |
| PD1/TGFβRII (with a final concentration of 5 μg/mL) | 7.90 ± 3.47 | 3.09 ± 0.24 | 2434.95 ± 221.71 | 0.38 ± 0.00 | 2.65 ± 0.22 | 1.70 ± 0.00 |

As can be seen from the results in the above table, the PD1/TGFβRII fusion protein of the present disclosure exhibits a low probability of causing a cytokine storm. Therefore, the subject substantially has no risk of systemic inflammation caused by overactivating the immune system after administration.

Example 10: Toxicity Assay of PD1/TGFβRII
Fusion Protein in Cynomolgus Monkeys

Single-dose toxicity: In this test, 4 cynomolgus monkeys were divided into two groups of 2, half male and half female in each group. Two groups of the monkeys were injected intravenously with a single dose of 200 mg/kg or 500 mg/kg of the PD1/TGFβRII fusion protein according to the present disclosure, respectively, and observed for 14 days. During the test, general observation was conducted, and parameters such as body weight, food intake, body temperature, II-lead ECG and blood pressure, hematology, blood biochemistry, and urine were detected. The gross anatomical observation was performed at the end of study.

After administration, the food intake of male monkeys in each group decreased transiently and recovered on Days 8 to 9 of the test. On day 14 of the test, RBC, HGB and HCT were reduced in male monkeys in each group. In addition, no obvious abnormal change was found in other indexes. In the single dose toxicity test, cynomolgus monkeys were injected intravenously with a single dose of 200 mg/kg or 500 mg/kg of the PD1/TGFβRII fusion protein according to the present disclosure, and MTD was 500 mg/kg.

Repeat-dose toxicity: In this test, 40 cynomolgus monkeys were divided into 4 groups of 10, half male and half female in each group, i.e., the blank control group and the treatment groups receiving 15 mg/kg, 50 mg/kg and 150 mg/kg of the PD1/TGFβRII fusion protein according to the present disclosure. The drug was administered once a week for 4 weeks (5 doses in total). After administration was finished, the monkeys were observed for 4 weeks.

A decrease in RBC, HGB and HCT, and a compensatory increase in RET and RET % can be found in the male monkeys in the 50 mg/kg group and the male and female monkeys in the 150 mg/kg group on Day 15 of administration and at the end of administration; on day 15 of administration, the above changes can also be found in the female monkeys in the 50 mg/kg group.

At the end of the administration, heart pericardial adhesions can be found in the gross anatomy of 1 male monkey in the 50 mg/kg group. Histopathological examination: very mild to mild mononuclear cell infiltration in cerebral meninges and choroid plexus, cerebellar meninges and choroid plexus, spinal cord ridge membrane, thyroid gland, heart and pituitary gland, and very mild to moderate vascular and/or perivascular inflammation in heart, liver, bladder, epididymis, seminal vesicles can be found in the cynomolgus monkeys in the 150 mg/kg group; very mild to moderate mononuclear cell infiltration in cerebral meninges, sciatic nerve, thyroid gland, heart and pituitary gland, and very mild to moderate vascular and/or perivascular inflammation in heart, bladder, duodenum, ileum, rectum, fallopian tube, vagina, uterine can be found in the cynomolgus monkeys in the 50 mg/kg group; very mild to mild mononuclear cell infiltration in cerebral meninges and choroid plexus, cerebellar choroid plexus, sciatic nerve, thyroid gland and heart, and mild vascular and/or perivascular inflammation in heart can be found in the cynomolgus monkeys in the 15 mg/kg group. In addition, 1 cynomolgus monkey in the 50 mg/kg and 150 mg/kg groups respectively had mild femoral necrosis and epiphysical plate thickening, and very mild to mild femoral metaphyseal trabecula and osteoclast increase.

In addition, no dead or dying animals were found, the cynomolgus monkeys in each group were all in good general conditions, and no obvious abnormal changes were found in body weight, food intake, body temperature, II-lead electrocardiogram, respiratory frequency, serum chemistry, ophthalmologic examination, urine examination, bone marrow smear, organ weight and coefficient, immune related indexes such as IgA, IgM, IgG, C3, C4, CIC and lymphocyte subpopulation, as well as TSH, T3, T4 and organ weight and coefficient.

In the repeat-dose toxicity test, cynomolgus monkeys were injected intravenously with 15 mg/kg, 50 mg/kg or 150 mg/kg of the PD1/TGFβRII fusion protein according to the present disclosure (once a week for 4 weeks, 5 doses in total), and HNSTD (highest non-severely toxic dose) was 150 mg/kg. According to the information disclosed in the Assessment report of Nivolumab in the European Medicines Agency, it is reasoned that the HNSTD of Nivolumab should be 50 mg/kg, which is much lower than the HNSTD of the PD1/TGFβRII fusion protein according to the present disclosure. As can be seen, the PD1/TGFβRII fusion protein according to the present disclosure shows low toxicity. Therefore, it can be expected that said fusion protein can show good safety in clinic use.

Although the present disclosure has been described in detail with respect to the general description and the specific embodiments above, it will be apparent to those skilled in the art that modifications and improvements can be made based on the present disclosure. Accordingly, these modifications or improvements made without departing from the spirit of the present disclosure fall within the scope of protection of the present disclosure.

The invention claimed is:

1. A bifunctional protein, comprising a PD-1 (programmed death receptor-1) binding moiety and a TGF-β (transforming growth factor-β) binding moiety, wherein the bifunctional protein comprises: (1) two identical first polypeptides, the amino acid sequence of the first polypeptide comprising the amino acid sequence set forth in SEQ ID NO: 13; and (2) two identical second polypeptides, the amino acid sequence of the second polypeptide comprising the amino acid sequence set forth in SEQ ID NO: 14.

2. A pharmaceutical composition, comprising the bifunctional protein according to claim 1 and a pharmaceutically acceptable excipient, diluent or carrier.

3. A bifunctional protein, comprising a PD-1 (programmed death receptor-1) binding moiety and a TGF-β (transforming growth factor-β) binding moiety, wherein the bifunctional protein comprises: a first polypeptide, the amino acid sequence of the first polypeptide comprising the amino acid sequence set forth in SEQ ID NO: 13; and a second polypeptide, the amino acid sequence of the second polypeptide comprising the amino acid sequence set forth in SEQ ID NO: 14.

* * * * *

SEQUENCE LISTING

```
<160> NUMBER OF SEQ ID NOS: 22

<210> SEQ ID NO 1
<211> LENGTH: 8
<212> TYPE: PRT
<213> ORGANISM: Artificial Sequence
<220> FEATURE:
<223> OTHER INFORMATION: Synthetized HCDR1 of anti-PD-1 antibody

<400> SEQUENCE: 1

Gly Phe Ala Phe Ser Ser Tyr Asp
1               5

<210> SEQ ID NO 2
<211> LENGTH: 8
<212> TYPE: PRT
```

-continued

<210> ORGANISM: Artificial Sequence
<220> FEATURE:
<223> OTHER INFORMATION: Synthetized HCDR2 of anti-PD-1 antibody

<400> SEQUENCE: 2

Ile Ser Gly Gly Gly Arg Tyr Thr
1               5

<210> SEQ ID NO 3
<211> LENGTH: 11
<212> TYPE: PRT
<213> ORGANISM: Artificial Sequence
<220> FEATURE:
<223> OTHER INFORMATION: Synthetized HCDR3 of anti-PD-1 antibody

<400> SEQUENCE: 3

Ala Asn Arg Tyr Gly Glu Ala Trp Phe Ala Tyr
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Synthetized LCDR1 of anti-PD-1 antibody

<400> SEQUENCE: 4

Gln Asp Ile Asn Thr Tyr
1               5

<210> SEQ ID NO 5
<211> LENGTH: 3
<212> TYPE: PRT
<213> ORGANISM: Artificial Sequence
<220> FEATURE:
<223> OTHER INFORMATION: Synthetized LCDR2 of anti-PD-1 antibody

<400> SEQUENCE: 5

Arg Ala Asn
1

<210> SEQ ID NO 6
<211> LENGTH: 9
<212> TYPE: PRT
<213> ORGANISM: Artificial Sequence
<220> FEATURE:
<223> OTHER INFORMATION: Synthetized LCDR3 of anti-PD-1 antibody

<400> SEQUENCE: 6

Leu Gln Tyr Asp Glu Phe Pro Leu Thr
1               5

<210> SEQ ID NO 7
<211> LENGTH: 118
<212> TYPE: PRT
<213> ORGANISM: Artificial Sequence
<220> FEATURE:
<223> OTHER INFORMATION: Synthetized VH of anti-PD-1 antibody

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Gly Leu Asp Trp Val
        35                  40                  45

-continued

```
Ala Thr Ile Ser Gly Gly Gly Arg Tyr Thr Tyr Tyr Pro Asp Ser Val
    50              55              60

Lys Gly Arg Phe Thr Ile Ser Arg Asp Asn Ser Lys Asn Asn Leu Tyr
65              70              75              80

Leu Gln Met Asn Ser Leu Arg Ala Glu Asp Thr Ala Leu Tyr Tyr Cys
                85              90              95

Ala Asn Arg Tyr Gly Glu Ala Trp Phe Ala Tyr Trp Gly Gln Gly Thr
            100             105             110

Leu Val Thr Val Ser Ser
        115
```

<210> SEQ ID NO 8
<211> LENGTH: 107
<212> TYPE: PRT
<213> ORGANISM: Artificial Sequence
<220> FEATURE:
<223> OTHER INFORMATION: Synthetized VL of anti-PD-1 antibody

<400> SEQUENCE: 8

```
Asp Ile Gln Met Thr Gln Ser Pro Ser Ser Met Ser Ala Ser Val Gly
1               5               10              15

Asp Arg Val Thr Phe Thr Cys Arg Ala Ser Gln Asp Ile Asn Thr Tyr
            20              25              30

Leu Ser Trp Phe Gln Gln Lys Pro Gly Lys Ser Pro Lys Thr Leu Ile
        35              40              45

Tyr Arg Ala Asn Arg Leu Val Ser Gly Val Pro Ser Arg Phe Ser Gly
    50              55              60

Ser Gly Ser Gly Gln Asp Tyr Thr Leu Thr Ile Ser Ser Leu Gln Pro
65              70              75              80

Glu Asp Met Ala Thr Tyr Tyr Cys Leu Gln Tyr Asp Glu Phe Pro Leu
                85              90              95

Thr Phe Gly Ala Gly Thr Lys Leu Glu Leu Lys
            100             105
```

<210> SEQ ID NO 9
<211> LENGTH: 330
<212> TYPE: PRT
<213> ORGANISM: Artificial Sequence
<220> FEATURE:
<223> OTHER INFORMATION: Synthetized Heavy chain constant region of
      anti-PD-1 antibody

<400> SEQUENCE: 9

```
Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
                85              90              95

Lys Val Glu Pro Lys Ser Cys Asp Lys Thr His Thr Cys Pro Pro Cys
            100             105             110
```

-continued

```
Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Ala
                325                 330

<210> SEQ ID NO 10
<211> LENGTH: 107
<212> TYPE: PRT
<213> ORGANISM: Artificial Sequence
<220> FEATURE:
<223> OTHER INFORMATION: Synthetized Light chain constant region of
      anti-PD-1 antibody

<400> SEQUENCE: 10

Arg Thr Val Ala Ala Pro Ser Val Phe Ile Phe Pro Pro Ser Asp Glu
1                   5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 11
<211> LENGTH: 136
<212> TYPE: PRT
<213> ORGANISM: Homo sapiens
```

<400> SEQUENCE: 11

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp
    130                 135
```

<210> SEQ ID NO 12
<211> LENGTH: 21
<212> TYPE: PRT
<213> ORGANISM: Artificial Sequence
<220> FEATURE:
<223> OTHER INFORMATION: Synthetized flexible linker

<400> SEQUENCE: 12

```
Gly Gly Gly Gly Ser Gly Gly Gly Gly Ser Gly Gly Gly Gly Ser Gly
1               5                   10                  15

Gly Gly Gly Ser Gly
            20
```

<210> SEQ ID NO 13
<211> LENGTH: 605
<212> TYPE: PRT
<213> ORGANISM: Artificial Sequence
<220> FEATURE:
<223> OTHER INFORMATION: Synthetized heavy chain portion of PD-1/TGF-
      Beta bifunctional protein

<400> SEQUENCE: 13

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Gly Leu Asp Trp Val
        35                  40                  45

Ala Thr Ile Ser Gly Gly Gly Arg Tyr Thr Tyr Tyr Pro Asp Ser Val
    50                  55                  60

Lys Gly Arg Phe Thr Ile Ser Arg Asp Asn Ser Lys Asn Asn Leu Tyr
65                  70                  75                  80

Leu Gln Met Asn Ser Leu Arg Ala Glu Asp Thr Ala Leu Tyr Tyr Cys
                85                  90                  95

Ala Asn Arg Tyr Gly Glu Ala Trp Phe Ala Tyr Trp Gly Gln Gly Thr
            100                 105                 110

Leu Val Thr Val Ser Ser Ala Ser Thr Lys Gly Pro Ser Val Phe Pro
```

-continued

```
              115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Ala
    435                 440                 445

Gly Gly Gly Gly Ser Gly Gly Gly Ser Gly Gly Gly Ser Gly
    450                 455                 460

Gly Gly Gly Ser Gly Ile Pro Pro His Val Gln Lys Ser Val Asn Asn
465                 470                 475                 480

Asp Met Ile Val Thr Asp Asn Asn Gly Ala Val Lys Phe Pro Gln Leu
                485                 490                 495

Cys Lys Phe Cys Asp Val Arg Phe Ser Thr Cys Asp Asn Gln Lys Ser
                500                 505                 510

Cys Met Ser Asn Cys Ser Ile Thr Ser Ile Cys Glu Lys Pro Gln Glu
                515                 520                 525

Val Cys Val Ala Val Trp Arg Lys Asn Asp Glu Asn Ile Thr Leu Glu
    530                 535                 540
```

Thr Val Cys His Asp Pro Lys Leu Pro Tyr His Asp Phe Ile Leu Glu
545                 550                 555                 560

Asp Ala Ala Ser Pro Lys Cys Ile Met Lys Glu Lys Lys Pro Gly
                565                 570                 575

Glu Thr Phe Phe Met Cys Ser Cys Ser Ser Asp Glu Cys Asn Asp Asn
                580                 585                 590

Ile Ile Phe Ser Glu Glu Tyr Asn Thr Ser Asn Pro Asp
        595                 600                 605

<210> SEQ ID NO 14
<211> LENGTH: 214
<212> TYPE: PRT
<213> ORGANISM: Artificial Sequence
<220> FEATURE:
<223> OTHER INFORMATION: Synthetized light chain portion of PD-1/TGF-
      Beta bifunctional protein

<400> SEQUENCE: 14

Asp Ile Gln Met Thr Gln Ser Pro Ser Ser Met Ser Ala Ser Val Gly
1               5                   10                  15

Asp Arg Val Thr Phe Thr Cys Arg Ala Ser Gln Asp Ile Asn Thr Tyr
                20                  25                  30

Leu Ser Trp Phe Gln Gln Lys Pro Gly Lys Ser Pro Lys Thr Leu Ile
        35                  40                  45

Tyr Arg Ala Asn Arg Leu Val Ser Gly Val Pro Ser Arg Phe Ser Gly
        50                  55                  60

Ser Gly Ser Gly Gln Asp Tyr Thr Leu Thr Ile Ser Ser Leu Gln Pro
65                  70                  75                  80

Glu Asp Met Ala Thr Tyr Tyr Cys Leu Gln Tyr Asp Glu Phe Pro Leu
                85                  90                  95

Thr Phe Gly Ala Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 15
<211> LENGTH: 1815
<212> TYPE: DNA
<213> ORGANISM: Artificial Sequence
<220> FEATURE:
<223> OTHER INFORMATION: Synthetized encoding sequence of heavy chain
      portion of PD-1/TGF-Beta bifunctional protein

<400> SEQUENCE: 15
gaggtacaac tggtggaatc cggtggcggt ctcgtgcagc ctggcggcag cctgagactg      60

-continued

```
agttgtgctg cttctggctt tgccttctcc tcctacgaca tgtcctgggt gcggcaggcc      120
cctggaaagg gcctggattg ggtggccacc atttccggag gcggcagata cacctactac      180
cctgactctg tcaagggccg gttcaccatc tccagagaca actccaagaa caacctgtac      240
ctgcagatga actccctgag agccgaggac accgccctgt actactgcgc caaccggtac      300
ggcgaggctt ggttcgccta ctggggccaa ggcaccctcg tgaccgtatc atccgcctcc      360
acaaagggcc cttctgtgtt ccctctggcc ccttcctcca agtctacaag cggaggcacc      420
gctgctctgg gctgcctggt caaggactac ttccccgaac ccgtgaccgt gtcttggaac      480
tccggcgctc tgacctctgg agtgcatacc ttccctgccg tgctgcagtc ctccggcctg      540
tactctctgt ccagcgtggt caccgtgcct agcagcagtc tgggaaccca gacatacatc      600
tgcaacgtga accacaagcc ctccaataca aaagtggaca gaaggtggga cctaaatcc       660 tgcgacaaga cccacacctg tcctccttgc cctgctcctg aggccgctgg cgcccctct       720 gtgtttctgt tccccctaa gcccaaggac accctgatga tctcccggac ccccgaggtg       780
acctgcgtgg tggtggacgt gtcccacgag gaccctgaag tgaagttcaa ctggtacgtg      840
gatggcgtgg aagtgcacaa cgccaagacc aagcctagag aggagcagta caacagcacc      900
tacagagtgg tctccgtgct gaccgttctg caccaggact ggctgaacgg caaggagtac      960
aagtgcaagg tgtccaacaa ggccctgccc gcccctatcg agaagaccat ctctaaggct     1020
aagggccagc ctagagaacc tcaagtgtac accctgcctc catctcggga tgagctgaca     1080
aagaatcagg tgtctctgac ctgtctggtg aagggcttct accctctga catcgccgtg      1140 gagtgggagt ctaacggcca gcccgagaac aactacaaga ccacccctcc tgtgctggac     1200
tccgacggct ccttcttcct gtactccaag ctgaccgtgg acaagtctag atggcagcag     1260
ggcaacgtgt tctcctgctc cgtgatgcac gaggccctgc acaaccacta cacacagaaa     1320
tccctgtccc tgtcccctgg cgctggaggc ggtggctccg gcggcggcgg ctccggtggc     1380
ggaggctccg gaggcggcgg ctctggcatc cccctcacg tgcagaagag cgtcaacaac     1440
gatatgatcg tgaccgacaa caacggagct gtgaagtttc tcaactgtg caagttctgc     1500 gacgtcagat tctctacctg tgataaccag aagtcctgca tgtccaactg cagcatcacc     1560
tccatctgcg agaaacctca agaggtgtgc gtggctgtgt ggcggaagaa cgacgaaaac     1620
atcaccctgg aaaccgtatg tcacgatcct aagctgcctt accacgactt catcctggaa     1680
gatgccgcct ctcccaagtg catcatgaaa gagaagaaga aacccggcga gacctttttc     1740
atgtgctctt gctccagcga cgagtgcaac gacaatatca tcttcagcga ggaatacaac     1800
accagcaacc tgac                                                       1815
```

```
<210> SEQ ID NO 16
<211> LENGTH: 642
<212> TYPE: DNA
<213> ORGANISM: Artificial Sequence
<220> FEATURE:
<223> OTHER INFORMATION: Synthetized encoding sequence of light chain
      portion of PD-1/TGF-Beta bifunctional protein

<400> SEQUENCE: 16
```

```
gatatccaga tgacccagtc ccctcctcc atgtccgcct ccgtgggcga cagagtgacc       60
ttcacctgca gagcttctca ggacatcaac acctacctgt cctggttcca gcagaagcct      120
ggcaagtctc ctaagaccct gatctacaga gccaaccggc tggtgtccgg cgtgccttct      180
cggttctccg gatctggctc tggccaggat tacaccctga ccatctcctc tctgcagcct      240
```

-continued

```
gaggacatgg ccacctacta ctgcctgcag tacgacgagt ccctctgac attcggcgct        300 ggcaccaagc tggaactgaa gcggaccgtg gccgctccta gcgtgttcat cttccctcct        360
tccgacgaac aactgaagtc cggcaccgcc tctgtggtgt gcctgctgaa caacttctac        420
cctagagagg ccaaggtgca gtggaaggtg acaacgccc tgcaaagcgg caactcccaa         480
gagtccgtca ccgagcagga cagcaaggac tccacctact ccctgtcttc tacactgacc        540
ctgtccaagg ccgactacga gaagcacaag gtgtacgcct gcgaggtgac acaccagggc        600
ctgagctccc ctgtgaccaa gtccttcaac agaggcgagt gc                          642
```

```
<210> SEQ ID NO 17
<211> LENGTH: 440
<212> TYPE: PRT
<213> ORGANISM: Artificial Sequence
<220> FEATURE:
<223> OTHER INFORMATION: Synthetized heavy chain of Nivolumab

<400> SEQUENCE: 17

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
```

-continued

```
        290                    295                    300

Asp Trp Leu Asn Gly Lys Glu Tyr Lys Cys Lys Val Ser Asn Lys Gly
305                    310                    315                    320

Leu Pro Ser Ser Ile Glu Lys Thr Ile Ser Lys Ala Lys Gly Gln Pro
                   325                    330                    335

Arg Glu Pro Gln Val Tyr Thr Leu Pro Pro Ser Gln Glu Glu Met Thr
                   340                    345                    350

Lys Asn Gln Val Ser Leu Thr Cys Leu Val Lys Gly Phe Tyr Pro Ser
                   355                    360                    365

Asp Ile Ala Val Glu Trp Glu Ser Asn Gly Gln Pro Glu Asn Asn Tyr
                   370                    375                    380

Lys Thr Thr Pro Pro Val Leu Asp Ser Asp Gly Ser Phe Phe Leu Tyr
385                    390                    395                    400

Ser Arg Leu Thr Val Asp Lys Ser Arg Trp Gln Glu Gly Asn Val Phe
                   405                    410                    415

Ser Cys Ser Val Met His Glu Ala Leu His Asn His Tyr Thr Gln Lys
                   420                    425                    430

Ser Leu Ser Leu Ser Leu Gly Lys
                   435                    440

<210> SEQ ID NO 18
<211> LENGTH: 214
<212> TYPE: PRT
<213> ORGANISM: Artificial Sequence
<220> FEATURE:
<223> OTHER INFORMATION: Synthetized light chain of Nivolumab

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
```

210

<210> SEQ ID NO 19
<211> LENGTH: 448
<212> TYPE: PRT
<213> ORGANISM: Artificial Sequence
<220> FEATURE:
<223> OTHER INFORMATION: Synthetized heavy chain of PD1 monoclonal
      antibody in CN106977602

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Gly Leu Asp Trp Val
        35                  40                  45

Ala Thr Ile Ser Gly Gly Gly Arg Tyr Thr Tyr Tyr Pro Asp Ser Val
    50                  55                  60

Lys Gly Arg Phe Thr Ile Ser Arg Asp Asn Ser Lys Asn Asn Leu Tyr
65                  70                  75                  80

Leu Gln Met Asn Ser Leu Arg Ala Glu Asp Thr Ala Leu Tyr Tyr Cys
                85                  90                  95

Ala Asn Arg Tyr Gly Glu Ala Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

```
Pro Pro Ser Arg Asp Glu Leu Thr Lys Asn Gln Val Ser Leu Thr Cys
        355             360             365

Leu Val Lys Gly Phe Tyr Pro Ser Asp Ile Ala Val Glu Trp Glu Ser
        370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Lys Leu Thr Val Asp Lys Ser
                405             410             415

Arg Trp Gln Gln Gly Asn Val Phe Ser Cys Ser Val Met His Glu Ala
                420             425             430

Leu His Asn His Tyr Thr Gln Lys Ser Leu Ser Leu Ser Pro Gly Lys
        435             440             445
```

```
<210> SEQ ID NO 20
<211> LENGTH: 597
<212> TYPE: PRT
<213> ORGANISM: Artificial Sequence
<220> FEATURE:
<223> OTHER INFORMATION: Synthetized heavy chain portion of
      Nivolumab/TGF-Beta-RII bifunctional protein

<400> SEQUENCE: 20
```

```
Gln Val Gln Leu Val Glu Ser Gly Gly Gly Val Val Gln Pro Gly Arg
1               5               10              15

Ser Leu Arg Leu Asp Cys Lys Ala Ser Gly Ile Thr Phe Ser Asn Ser
        20              25              30

Gly Met His Trp Val Arg Gln Ala Pro Gly Lys Gly Leu Glu Trp Val
        35              40              45

Ala Val Ile Trp Tyr Asp Gly Ser Lys Arg Tyr Tyr Ala Asp Ser Val
        50              55              60

Lys Gly Arg Phe Thr Ile Ser Arg Asp Asn Ser Lys Asn Thr Leu Phe
65              70              75              80

Leu Gln Met Asn Ser Leu Arg Ala Glu Asp Thr Ala Val Tyr Tyr Cys
                85              90              95

Ala Thr Asn Asp Asp Tyr Trp Gly Gln Gly Thr Leu Val Thr Val Ser
                100             105             110

Ser Ala Ser Thr Lys Gly Pro Ser Val Phe Pro Leu Ala Pro Cys Ser
        115             120             125

Arg Ser Thr Ser Glu Ser Thr Ala Ala Leu Gly Cys Leu Val Lys Asp
        130             135             140

Tyr Phe Pro Glu Pro Val Thr Val Ser Trp Asn Ser Gly Ala Leu Thr
145             150             155             160

Ser Gly Val His Thr Phe Pro Ala Val Leu Gln Ser Ser Gly Leu Tyr
                165             170             175

Ser Leu Ser Ser Val Val Thr Val Pro Ser Ser Ser Leu Gly Thr Lys
        180             185             190

Thr Tyr Thr Cys Asn Val Asp His Lys Pro Ser Asn Thr Lys Val Asp
        195             200             205

Lys Arg Val Glu Ser Lys Tyr Gly Pro Pro Cys Pro Pro Cys Pro Ala
        210             215             220

Pro Glu Phe Leu Gly Gly Pro Ser Val Phe Leu Phe Pro Pro Lys Pro
225             230             235             240

Lys Asp Thr Leu Met Ile Ser Arg Thr Pro Glu Val Thr Cys Val Val
                245             250             255

Val Asp Val Ser Gln Glu Asp Pro Glu Val Gln Phe Asn Trp Tyr Val
                260             265             270
```

-continued

```
Asp Gly Val Glu Val His Asn Ala Lys Thr Lys Pro Arg Glu Glu Gln
    275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
                340                 345                 350

Lys Asn Gln Val Ser Leu Thr Cys Leu Val Lys Gly Phe Tyr Pro Ser
                355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
                420                 425                 430

Ser Leu Ser Leu Ser Leu Gly Ala Gly Gly Gly Ser Gly Gly Gly
                435                 440                 445

Gly Ser Gly Gly Gly Gly Ser Gly Gly Gly Gly Ser Gly Ile Pro Pro
    450                 455                 460

His Val Gln Lys Ser Val Asn Asn Asp Met Ile Val Thr Asp Asn Asn
465                 470                 475                 480

Gly Ala Val Lys Phe Pro Gln Leu Cys Lys Phe Cys Asp Val Arg Phe
                485                 490                 495

Ser Thr Cys Asp Asn Gln Lys Ser Cys Met Ser Asn Cys Ser Ile Thr
                500                 505                 510

Ser Ile Cys Glu Lys Pro Gln Glu Val Cys Val Ala Val Trp Arg Lys
                515                 520                 525

Asn Asp Glu Asn Ile Thr Leu Glu Thr Val Cys His Asp Pro Lys Leu
    530                 535                 540

Pro Tyr His Asp Phe Ile Leu Glu Asp Ala Ala Ser Pro Lys Cys Ile
545                 550                 555                 560

Met Lys Glu Lys Lys Lys Pro Gly Glu Thr Phe Phe Met Cys Ser Cys
                565                 570                 575

Ser Ser Asp Glu Cys Asn Asp Asn Ile Ile Phe Ser Glu Glu Tyr Asn
                580                 585                 590

Thr Ser Asn Pro Asp
        595
```

```
<210> SEQ ID NO 21
<211> LENGTH: 446
<212> TYPE: PRT
<213> ORGANISM: Artificial Sequence
<220> FEATURE:
<223> OTHER INFORMATION: Synthetized heavy chain of IgG1 protein

<400> SEQUENCE: 21

Glu Val Gln Leu Glu Gln Ser Gly Ala Glu Leu Met Lys Pro Gly Ala
1               5                   10                  15

Ser Val Lys Ile Ser Cys Lys Ala Thr Gly Tyr Thr Phe Thr Thr Tyr
                20                  25                  30
```

-continued

```
Trp Ile Glu Trp Ile Lys Gln Arg Pro Gly His Ser Leu Glu Trp Ile
        35              40              45

Gly Glu Ile Leu Pro Gly Ser Asp Ser Thr Tyr Tyr Asn Glu Lys Val
    50              55              60

Lys Gly Lys Val Thr Phe Thr Ala Asp Ala Ser Ser Asn Thr Ala Tyr
65              70              75              80

Met Gln Leu Ser Ser Leu Thr Ser Glu Asp Ser Ala Val Tyr Tyr Cys
                85              90              95

Ala Arg Gly Asp Gly Phe Tyr Val Tyr Trp Gly Gln Gly Thr Thr Leu
            100             105             110

Thr Val Ser Ser Ala Ser Thr Lys Gly Pro Ser Val Phe Pro Leu Ala
            115             120             125

Pro Ser Ser Lys Ser Thr Ser Gly Gly Thr Ala Ala Leu Gly Cys Leu
        130             135             140

Val Lys Asp Tyr Phe Pro Glu Pro Val Thr Val Ser Trp Asn Ser Gly
145             150             155             160

Ala Leu Thr Ser Gly Val His Thr Phe Pro Ala Val Leu Gln Ser Ser
                165             170             175

Gly Leu Tyr Ser Leu Ser Ser Val Val Thr Val Pro Ser Ser Ser Leu
            180             185             190

Gly Thr Gln Thr Tyr Ile Cys Asn Val Asn His Lys Pro Ser Asn Thr
            195             200             205

Lys Val Asp Lys Lys Val Glu Pro Lys Ser Cys Asp Lys Thr His Thr
        210             215             220

Cys Pro Pro Cys Pro Ala Pro Glu Leu Leu Gly Gly Pro Ser Val Phe
225             230             235             240

Leu Phe Pro Pro Lys Pro Lys Asp Thr Leu Met Ile Ser Arg Thr Pro
                245             250             255

Glu Val Thr Cys Val Val Val Asp Val Ser His Glu Asp Pro Glu Val
            260             265             270

Lys Phe Asn Trp Tyr Val Asp Gly Val Glu Val His Asn Ala Lys Thr
        275             280             285

Lys Pro Arg Glu Glu Gln Tyr Asn Ser Thr Tyr Arg Val Val Ser Val
    290             295             300

Leu Thr Val Leu His Gln Asp Trp Leu Asn Gly Lys Glu Tyr Lys Cys
305             310             315             320

Lys Val Ser Asn Lys Ala Leu Pro Ala Pro Ile Glu Lys Thr Ile Ser
                325             330             335

Lys Ala Lys Gly Gln Pro Arg Glu Pro Gln Val Tyr Thr Leu Pro Pro
            340             345             350

Ser Arg Asp Glu Leu Thr Lys Asn Gln Val Ser Leu Thr Cys Leu Val
            355             360             365

Lys Gly Phe Tyr Pro Ser Asp Ile Ala Val Glu Trp Glu Ser Asn Gly
        370             375             380

Gln Pro Glu Asn Asn Tyr Lys Thr Thr Pro Pro Val Leu Asp Ser Asp
385             390             395             400

Gly Ser Phe Phe Leu Tyr Ser Lys Leu Thr Val Asp Lys Ser Arg Trp
                405             410             415

Gln Gln Gly Asn Val Phe Ser Cys Ser Val Met His Glu Ala Leu His
            420             425             430

Asn His Tyr Thr Gln Lys Ser Leu Ser Leu Ser Pro Gly Lys
            435             440             445
```

-continued

```
<210> SEQ ID NO 22
<211> LENGTH: 214
<212> TYPE: PRT
<213> ORGANISM: Artificial Sequence
<220> FEATURE:
<223> OTHER INFORMATION: Synthetized light chain of IgG1 protein

<400> SEQUENCE: 22

Asp Ile Glu Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Thr Ser Gln Ser Met Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Val Tyr Phe Cys Gln Gln Ser Gly Ser Trp Pro Arg
                85                  90                  95

Thr Phe Gly Gly Gly Thr Lys Leu Asp Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```